United States Patent [19]

Drake et al.

[11] Patent Number: 4,587,267

[45] Date of Patent: May 6, 1986

[54] CONTROLLED RELEASE SYSTEM

[75] Inventors: Cyril F. Drake, Harlow; Alfred J. Arch, Stansted, both of England

[73] Assignee: Standard Telephones and Cables, PLC, London, England

[21] Appl. No.: 650,045

[22] Filed: Sep. 13, 1984

[30] Foreign Application Priority Data

Sep. 15, 1983 [GB] United Kingdom ............... 8324784

[51] Int. Cl.⁴ .............................................. A61K 9/26
[52] U.S. Cl. ..................................... 514/769; 424/16; 424/19; 514/770; 514/953; 514/965; 604/890; 604/891; 604/892
[58] Field of Search .............. 514/770, 769, 953, 965; 604/890, 891, 892; 424/16, 19

[56] References Cited

U.S. PATENT DOCUMENTS

| | | | |
|---|---|---|---|
| 3,923,969 | 12/1975 | Baukal et al. | 514/770 |
| 4,123,248 | 10/1978 | Drake | 501/45 |
| 4,283,227 | 8/1981 | Drake | 424/162 |
| 4,349,025 | 9/1982 | Drake | 424/22 |
| 4,449,981 | 5/1984 | Drake et al. | 424/22 |
| 4,473,545 | 9/1984 | Drake et al. | 424/22 |

FOREIGN PATENT DOCUMENTS 2109665 6/1983 United Kingdom .
2111388 7/1983 United Kingdom .

*Primary Examiner*—Ronald W. Griffin
*Attorney, Agent, or Firm*—Dennis P. Clarke

[57] ABSTRACT

A device for the controlled release of an active material into an aqueous medium comprises a porous sintered body of a water soluble glass (11). The pores of the body are filled with a composition (12) consisting wholly or partially of an active material. The device may be provided with a low solubility coating (13). On immersion in an aqueous medium the glass (11) dissolves to become a sponge-like structure having a plurality of convoluted capillaries and from which the active material is released.

12 Claims, 5 Drawing Figures

CONTROLLED RELEASE SYSTEM

This invention relates to arrangements for providing the controlled release of an active material into an aqueous medium and to methods of manufacturing such compositions.

There is a broad range of applications wherein it is necessary to provide for the release of an active material at a controlled rate into an aqueous environment. In the biosciences, particularly, the potential for prolonging the action of numerous bioactive compounds is stimulating considerable interest.

Since the early 1950's researchers have attempted to develop controlled release systems able to store active materials and then release them at controlled rates into aqueous systems. This research has tended to concentrate on polymeric materials. Many polymers may be fabricated at relatively low temperatures to encapsulate effectively active materials thereby protecting them from unwanted interaction with the environment. Subsequent release of the active material is effected by one of four general mechanisms, i.e. diffusion, swelling, (bio) chemical action and magnetic processes. However, in most cases it has proved impractical to engineer the required degree of control, especially over long periods, and in many instances toxicity of the special polymer itself has limited exploitation.

Composite controlled release systems are known in which particulate soluble material dispersed in a significantly less soluble matrix are preferentially dissolved by a liquid medium to produce a network of capillaries through which an active material can then be released into solution. Typical of these systems are those described in our co-pending United Kingdom applications No. 2109665A (C. F. Drake-R. Jones 82-2) and No. 2111388A (C. F. Drake-R. Jones 83-3).

These types of controlled release systems suffer from the disadvantage that, if the particles of the soluble material are not each in contact with their neighbours then their continuous dissolution is interrupted by the inter-layer of less soluble matrix. This of course inhibits release of the active material to the liquid medium.

The object of the present invention is to minimise or to overcome this disadvantage.

According to one aspect of the invention there is provided a device for the controlled release of an active material into an aqueous medium in contact with the device, the device including a porous sintered body made from a particulate water soluble glass, the pores of said body containing a material comprising wholly or partially an active material.

According to another aspect of the invention there is provided a device for the controlled release of an active material into an aqueous medium in contact with the device, the device including a substantially insoluble tube open at at least one end and containing a composite material comprising a porous sintered body of a water soluble glass, the pores of said body containing a material comprising wholly or partially of an active material, wherein the dissolution rate of the glass is significantly less than that of the active material.

The term 'active material' as employed herein may include a medicament or therapeutic agent, a specific or non-specific biocidal material, a food, a food additive, a perfume, a pheromone or a fertiliser. Other materials include a water-snail attractant/poison, as well as materials selected to release inorganic substances for biological or non-biological applications. The inorganic materials may include, for example, Se as a trace nutrient for farm animals and inorganic and/or organic substances for protection of metals against corrosion.

The device may be provided in the form of a pill, tablet or implant, or in the form of a rumen bolus.

An embodiment of the invention will now be described with reference to the accompanying drawings in which.

Figure 1:
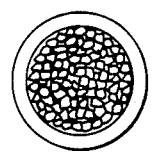
FIG. 1 is a cross sectional view of the controlled delivery device.
Figure 2:
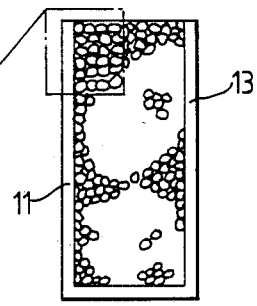
FIGS. 2, 3 and 4 illustrate on a larger scale the successive stages of dissolution of the device of FIG. 1.
Figure 2:
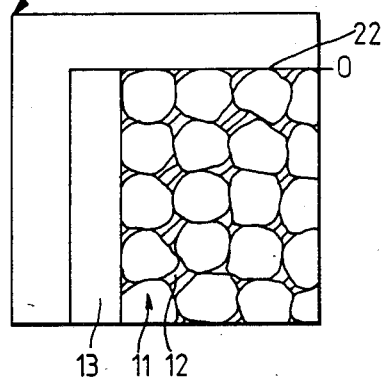
Figure 3:
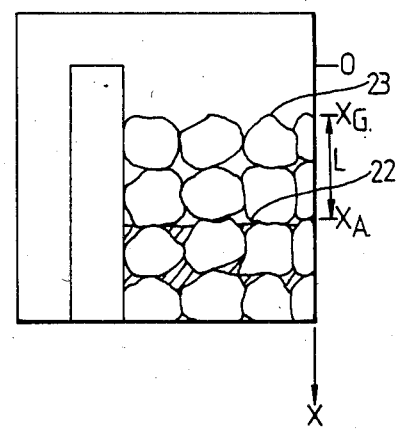
Figure 4:
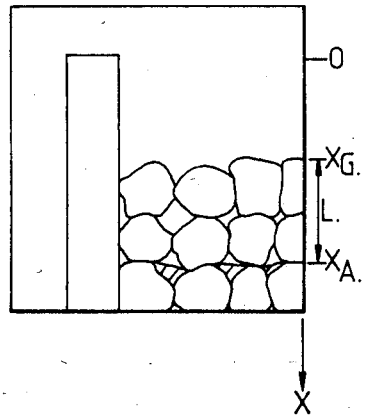

Referring to FIGS. 1-4, the device comprises a coherent porous body 11 of a sintered particulate water soluble glass in which the continuous cavities have a volume of 15 to 60% of the volume of the sintered body. The particle/size distribution of the glass, the method of forming the presinter body and the sintering conditions and the effect these have on the free volume of the device will be apparent to those skilled in the art.

The free space in the porous body so produced is filled with a composition 12 comprising partially or wholly of an active material. Depending on the nature of the active material the filling can be effected e.g. by absorbing the melted material which subsequently solidifies or by dissolving or dispersing the material in a low melting point carrier and soaking up the molten product. The body may optionally be provided with a low solubility coating 13.

The porous sintered body 11 can of course be manufactured in bulk and broken into suitably sized granules prior to filling with the active material, or it may be filled in bulk form and then granulated.

When the device is immersed in water the pore-filling material (12) exposed at the interface 22 (FIG. 2) will begin to dissolve. If the material 12 dissolves more rapidly than the glass then after a period t, the device will reach the stage shown in FIG. 3. The material 12 has been dissolved out from the pores to a depth L (FIG. 3) from the original surface and has been replaced by water. A small amount of glass will have been dissolved in this time t, and this is shown as o-$x_G$ FIG. 2.

At this stage the rate of solution of the material 12 will be limited by the fact that transport from the interface 22 is now mainly by diffusion. After the time t, at which time the diffusion path length is approximately equal to (but in fact somewhat greater than) L, the rate of transport of the water 12 to the bulk solution expressed in terms of the rate at which the interface 22 is advancing is now equal to the rate at which the glass dissolves, expressed as the rate at which the water/sinter glass interface 23 advances. This rate will henceforth remain constant as the rate of solution of the material 12 will be controlled by the rate of solution of the glass and, in fact, equal to the latter.

Figure 5:
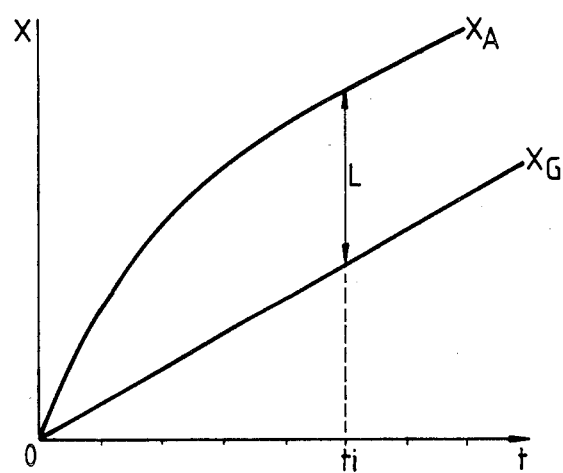
FIG. 5 show successive stages in the dissolution from a single capillary containing an active material.

FIG. 5 illustrates graphically the process described above. The water/glass interface 23 advances at a constant rate. The interface 22 initially advances very rapidly as the dissolution of the material 12 proceeds by mass flow of water over its surface, convectional transport, and diffusion over a short path. As the path length increases the first two processes play a rapidly decreasing role and the rate of diffusive transport falls with time as the diffusion path-length increases. When the slope of $x_A$ becomes equal to that of $x_G$ the value of $L = X_A - X_G$ remains constant henceforth and the rate of dissolution of 12 is now entirely controlled by the rate of solution of the glass.

The principle of this invention can be understood by considering the behaviour of an open-ended, insoluble, glass capillary filled with an active material which is to be delivered to the aqueous medium. It will be clear that the sintered-glass body can be considered as an assembly of very convoluted glass walled capillaries.

When the filled capillary is immersed in water, the filler will dissolve from the open ends of the capillary. The active material will be transferred to the bulk solution by diffusion and, initially, convection the 'stirring' of the bulk solution.

At a certain time after immersion in the aqueous medium. It is assumed that, at this stage, convection and physical movement of the solution no longer play a significant part in transport of the active material from the interface to the bulk solution. The rate at which the material is dissolved is now limited by diffusion and it can readily be shown that:

$$Q = A(2DC_o\rho)^{\frac{1}{2}} \cdot t^{\frac{1}{2}} \quad 1$$

where Q is the total mass of active material (g) that has dissolved at a time t (days)

D is the diffusion constant of the material in the aqueous medium, $cm^2 d^{-1}$.

$C_o$ is the solubility of the active material 62 in the aqueous medium, $g.cm^{-3}$.

$\rho$ is the density of the active material 62.

A is the area of cross section of capillary bore, $cm^2$.

t is the time, days.

The length of the column of the material $x_A$ dissolved at time t is given by:

$$x_A = (2DC_o)^{\frac{1}{2}} \cdot t^{\frac{1}{2}} \quad 2$$

For a typical value of the diffusion constant of moderate molecular weight materials in aqueous solution at room temperature, $D \sim 0.2 \, cm^2 d^{-1}$ and taking $\rho \sim 1$ and $C_o = 10^{-3} \, g.cm^{-3}$ (1 g/l)

$$x_A = 2 \times 10^{-2} t^{\frac{1}{2}}$$

Thus the length of active material dissolved in 1 day is 0.2 mm, and in 100 days 2 mm.

This outline calculation can be extended to the composite body in the form of a cylindrical rod of FIGS. 1-4 which, during dissolution, can be considered as a plurality of convoluted capillaries composed of a soluble glass. Neither the overall size of the body nor the absolute size of the pores is critical but the pores should be sufficiently small that convection within the pores should not after the initial period play a significant role in transporting dissolved material to the aqueous medium in which the device is immersed. The calculation is for a body coated with a water-insoluble, impervious, coating on all faces except the end face. When the body is placed in water, active material will dissolve from the pores, initially rapidly as the path length along the pores is small, at a rate at least equal to the diffusion-controlled rate $$\left(\frac{dx_A}{dt}\right)_{init.} = \left(\frac{DC_o}{2\rho t}\right)^{\frac{1}{2}} \quad 3$$

where $x_A$ is the distance from the bulk aqueous phase (glass/water interface) to the surface 23 (FIG. 2) of undissolved active material. This rate will decrease with time.

Simultaneously, the glass is dissolving at a constant rate R, $cm.d^{-1}$ and after a time $t_s$ when $$\frac{dx_G}{dt} = R$$

the rod will dissolve maintaining a constant distance L between the glass/water interface and the undissolved active material (FIG. 5).

The time $t_s$ is given by:

$$t_s = \frac{DC_o}{2\rho R^2} \quad 4$$

If $D = 0.2 \, cm^2.d^{-1}$, $C_o = 1$ g per liter, $\rho \sim 1$, $R = 10^{-2} \, cm.d^{-1}$ and the percentage volume of the rod occupied by active material is 32% then $t_s = 1$ day and the rod will dissolve at a uniform rate of $10^{-2} \, cm.d^{-1}$ over a period of 1000 days releasing 10 mg of active material 12 per day. The initial release of active material during the first day will be about 50 mg.

It is not of course necessary in all applications to encase the controlled delivery device in a low solubility coating. Thus, in one form of the device a composite block of porous sintered soluble glass is filled with molten, active material, is subsequently broken up into granules of an average diameter d of, e.g., 2 mm.

If the soluble glass is of a composition with a high differential rate of solution between acid and neutral aqueous solution, then when the granules are immersed in a neutral solution the glass will dissolve very slowly and the active material will reach the surrounding aqueous medium through the pores at a rate decreasing with time and given by Equation 4 above.

If the pH of the solution becomes more acid, e.g. if an acid active material is used, or the granules are transferred to a more acid solution, the rate of solution of the glass $R_1$ will now determine the rate at which the active material is released.

The following example illustrates the invention.

A glass was prepared by melting a batch of the composition

CaHPO$_4$: 17.8 g
NaH$_2$PO$_4$: 31.6 g
P$_2$O$_5$: 6.5 g in a platinum crucible. The batch was melted for half an hour in an air atmosphere in an electric muffle furnace at 1150° C. and the molten glass was periodically agitated. The melt was poured onto a cold steel plate and when cool ground to a fine powder. The composition of the final glass was (mole %) Na$_2$O, 26.2: CaO 26.0: P$_2$O$_5$ 47.9. The powdered glass was sieved and a fraction with particle size between 75-125 microns was used to prepare the sinter mass.

The powdered glass was packed by tamping into a steel mold with a 3 mm diameter cylindrical cavity and heated at 380° C. for 40 min. The resultant sintered rod had a porosity of 31% of free volume as calculated from its density.

A 4 mm length of the sintered rod was 'filled' with molten biological grade stearic acid by capillary action. The composite device was then leached in deionized water at 38° C. and after the rapid initial loss the uniform rate of solution settled down at 1.4 mg.cm$^{-2}$.h$^{-1}$ corresponding to a 'life' as a controlled release device of 4 days.

It will be clear that by using a glass of different solution rate this time could have been adjusted to any required value. For example by using a glass with the following composition the 'life' would have been about 30 days:

Na$_2$O, 22.5: CaO 32.5: P$_2$O$_5$ 45 (mole %).

It will also be clear that the stearic acid could be replaced by a meltable composition containing or consisting of an active material.

We claim:

1. A device for the controlled release of an active material into an aqueous medium in contact with the device, the device including a porous coherent body of a sintered particulate water soluble glass, the pores of said body being impregnated with a material comprising wholly or partially an active material, the device being such that, when contacted with the aqueous medium, the rate at which the active material is released into the medium is determined by the dissolution rate of the glass.

2. A device as claimed in claim 1 wholly or partly clad with a coating of relatively low dissolution rate.

3. A device as claimed in claim 1 or 2, wherein the active material includes selenium.

4. A device as claimed in claim 1 or 2, wherein the active material is selected from the group consisting of medicines and therapeutic agents.

5. A device as claimed in claim 4, wherein the active material is a hormone.

6. A device as claimed in claim 5, wherein the hormone is insulin.

7. A device as claimed in claim 5 wherein the hormone is progesterone.

8. A device as claimed in claim 1, wherein the active material includes a water snail attractant poison.

9. A device as claimed in claim 1, wherein the glass has a dissolution rate that is significantly dependent on the pH of an aqueous medium.

10. A device for the controlled release of an active material into an aqueous medium in contact with the device, the device including a substantially insoluble tube open at at least one end and containing a composite material comprising a porous coherent body of a sintered particulate water soluble glass, the pores of said body being impregnated with a material comprising wholly or partially of an active material, wherein the dissolution rate of the glass is significantly less than that of the active material, the device being such that, when contacted with the aqueous medium, the rate at which the active material is released into the medium is determined by the dissolution rate of the glass.

11. A pill, tablet or granule, incorporating a device as claimed in claim 1.

12. An implant or bolus incorporating a device as claimed in claim 1.

* * * * *